March 3, 1964 H. C. SWIM ETAL Plant Pat. 2,371
ROSE PLANT
Filed March 6, 1963
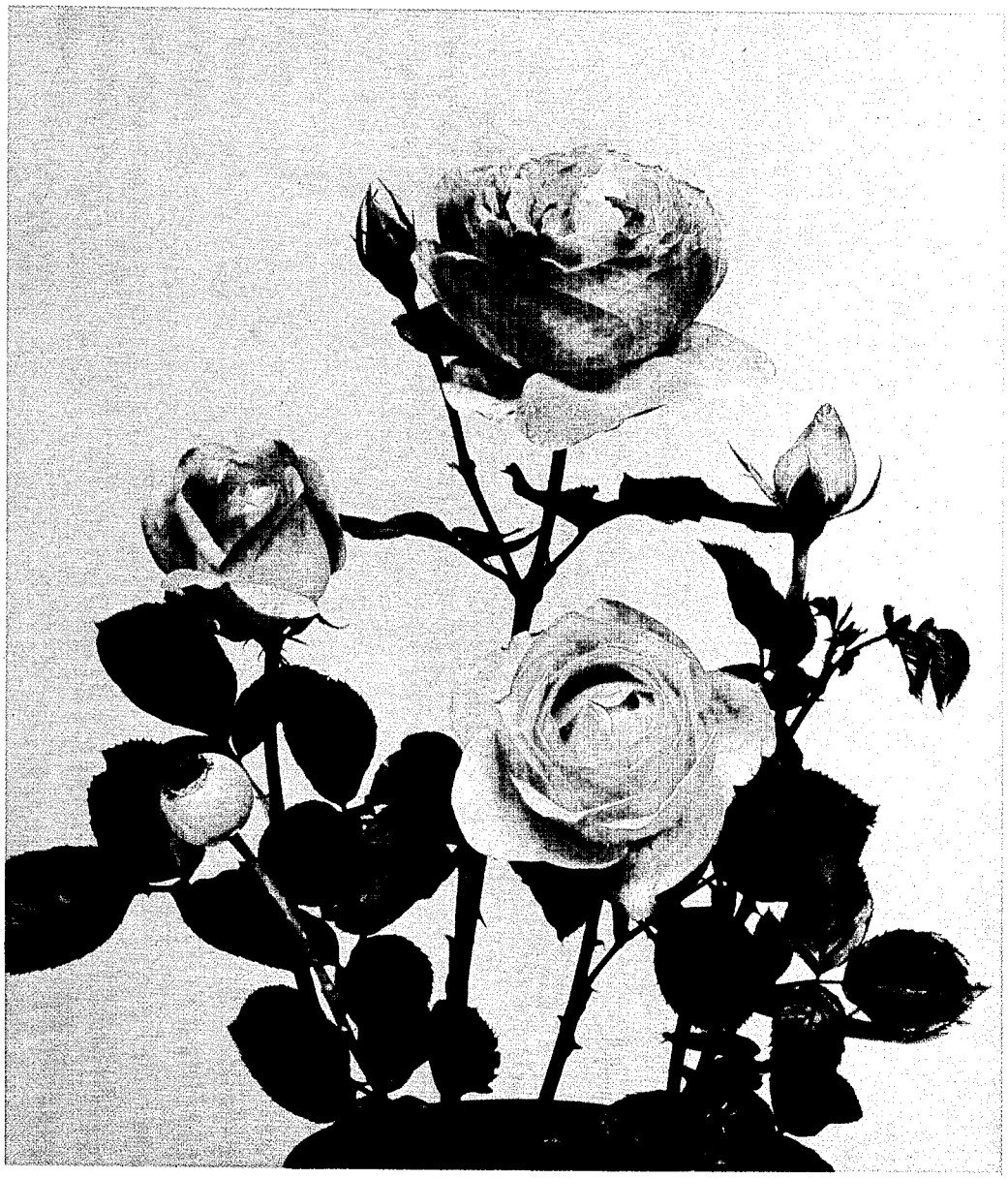
Inventors.
H. C. Swim and
O. L. Weeks
By: Robb & Robb
Attorneys.

United States Patent Office

Plant Pat. 2,371
Patented Mar. 3, 1964

2,371
ROSE PLANT

Herbert C. Swim, Ontario, and O. L. Weeks, Chino, Calif., assignors, by mesne assignments, to The Conrad-Pyle Company, West Grove, Pa., a corporation of Pennsylvania Filed Mar. 6, 1963, Ser. No. 263,365
1 Claim. (Cl. Plt.—17)

The present invention relates to a new and distinct variety of rose plant of the grandiflora class, which was originated by us by crossing the variety "Circus" (Plant Patent No. 1,382) with the variety "Queen Elizabeth" (Plant Patent No. 1,259).

As the result of this breeding, we have produced a new and improved rose variety which is endowed with the following unique combination of characteristics which are outstanding therein and which distinguish it from its parents, as well as from all other varieties of which we are aware:

(1) Vigorous, upright and tall habit of growth;

(2) Distinctive shape, medium to large size and distinctive surface appearance of the foliage as more particularly illustrated and described in the following description;

(3) A habit of producing the large majority of the flowers in both simple and compound clusters;

(4) Medium to large size and attractive shape of the flowers as illustrated and as hereinafter more particularly described;

(5) A distinctive and attractive general color tonality of the flowers corresponding to salmon color and which may be popularly described as shrimp color; and (6) A high degree of resistance of leaves and stems to powdery mildew when grown under the climatic conditions of southern California.

In comparison with its seed parent, "Circus," the new variety is substantially taller and approximately twice as tall when grown under comparable conditions; its leaves are larger and more flat; the flowers are substantially larger; the flower form is quite different and is cupped, usually with many petaloids in the center of the flower, as distinguished from the high-centered to flat flower form, with few or no petaloids in the case of the flowers of this parent; and the flower color is substantially different, corresponding to salmon or shrimp color, with varying shades of pink being dominant in the flowers, as distinguished from the multi-color yellow and red flowers of this parent in which the red color is dominant.

As compared with the pollen parent, "Queen Elizabeth," the plant height is much less; the foliage is substantially more flat; most of the flowers have many petaloids in their center, as distinguished from the very few petaloids found in the flower centers of this parent; the flower color is substantially different, being distinctly reddish salmon or shrimp color, as distinguished from the dominant pink of the flowers of this parent; and the flowers are fragrant, as distinguished from the flowers of this parent, which have no fragrance.

A sexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: Tall; bush; outdoor; primarily for garden decoration.

Class: Grandiflora.

Breeding: Seedling.

*Seed parent.*—"Circus."

*Pollen parent.*—"Queen Elizabeth."

Propagation: Holds its distinguishing characteristics through succeeding propagations by budding.

*Flower*

Locality where grown and observed: Ontario, California.

Flowers borne: From singly to several to stem; in irregular clusters; on stems of medium length and from normal strength to strong.

Quantity of bloom: From moderate to free, outdoors.

Continuity: More or less continuous during growing season.

Fragrance: Moderately penetrating. Nature—Spicy.

Bud:

*Peduncle.*—From short to medium length; medium caliper; erect; with numerous stipitate glands. Color—usually light green.

*Before calyx breaks.*—Size—medium. Form—short; ovoid; sometimes with a conspicuous neck; with foliaceous appendages on the surface of the bud; with slender foliaceous parts extending beyond the tip of the bud equal to ¼ or more of its length. Color—from Moderate Red, Plate 2.5R 4/10 to Dark Red, Plate 2.5R 3/7.

*As calyx breaks.*—Color—from Strong Red, Plate 2.5R 5/12 to Moderate Red, Plate 2.5R 4/10.

*As first petal opens.*—Size—medium. Form—ovoid. Color: outside—small area at base near Brilliant Greenish Yellow, Plate 7.5Y 9/8, quickly changing to near Pale Pink, Plate 2.5R 9/3 and progressing therebeyond through deeper shades of pink toward the margins which are near Deep Pink, Plate 10RP 6/12; inside—small area at base near Brilliant Greenish Yellow, Plate 7.5Y 9/8, quickly changing to near Moderate Pink, Plate 5R 8/6 and becoming near Deep Pink, Plate 2.5R 6/11, overlaid in varying degree with Strong Reddish Orange, Plate 7.5R 6/12 over upper ¾ of petal.

*Opening.*—Opens up well; is retarded from opening by cold and wet weather.

Bloom:

*Size (when fully open).*—From medium to large for class; from 3¾ inches to 4¼ inches.

*Petalage.*—Double; from 40 to 55 petals, with inner rows often but not invariably formed of 6 to 15 fragmentary petals; arranged regularly toward the outside.

*Form.*—Cupped at first and remaining cupped; cupped form not as pronounced at maturity as in the newly opened flower.

Petals:

*Texture.*—Thin; leathery.

*Appearance.*—Inside—satiny. Outside—shiny.

*Shape.*—Outside—nearly round, but cupped, with apex flat or only very slightly pointed. Intermediate—obovate-truncate, with apex flat, or very bluntly pointed. Inside—from fragmentary to varying shape, with varying amounts of vegetative markings.

This description of a newly opened flower was made from a rose grown outdoors during the month of October at Ontario, California:

*Color.*—Outer petal: outside surface—small area at base near Brilliant Greenish Yellow, Plate 7.5Y 9/8, quickly changing to Pale Pink, Plate 2.5R 9/3 and progressing therebeyond through deeper shades of pink towards the upper 4/5 of petal which is between Deep Pink, Plate 2.5R 6/11 and Strong Red, Plate 2.5R 5/12; inside surface—small area at base near brilliant Greenish Yellow, Plate 7.5Y 9/8, quickly changing to Deep Pink, Plate 10RP 6/12, faintly overlaid in varying degree with Strong Reddish Orange, Plate 7.5R 6/12. Intermediate petal: outside surface—base near Brilliant Greenish Yellow, Plate 7.5Y 9/8, changing to near white and then to a Pale Pink and quickly to a color between Deep Pink, Plate 10RP 6/12 and Strong Purplish Red, Plate 10RP 5/12, said latter color dominating about 4/5 of the upper portion of the petal, with the midrib and veins nearer Strong Purplish Red, Plate 10RP 5/12; inside surface—basal area near Greenish Yellow, Plate 7.5Y 9/8,, changing to near white and then to a basic color near Deep Pink, Plate 10RP 6/12, with veins and midrib of Strong Purplish Red, Plate 10RP 5/12. Inner petal: outside surface—Brilliant Greenish Yellow, Plate 7.5Y 9/8 at point of attachment, shading to a near white and thereafter to Deep Pink, Plate 10RP 6/12 over upper 4/5 of petal, with midrib of slightly deeper color; inside surface—Brilliant Greenish Yellow, Plate 7.5Y 9/8 at base, shading near white and then quickly to Strong Pink, Plate 10RP 7/8, with latter color covering about 4/5 of upper portion of petal.

This description was made from a rose that was open for three days outdoors during the month of October at Ontario, California:

*Color.*—Outer petal: outside surface—faint yellow at base, but dominantly near white in this area, quickly changing to between Deep Pink, Plate 10RP 6/12 and Strong Purplish Red, Plate 10RP 5/12, with midrib and veins having latter color; inside surface—faint yellow at base, but quickly changing to near white and then to Strong Purplish Red, Plate 10RP 5/12, overlaid faintly and variably with Vivid Red, Plate 5R 5/13. Inner petal: outside surface—area from base to ½ inch upward is near white, with remainder of petal near Deep Pink, Plate 10RP 6/12, and with midrib and veins faintly colored with Strong Purplish Red, Plate 10RP 5/12; inside surface—base near white, changing to basic color of near Strong Pink, Plate 10RP 7/8, but overlaid with from Deep Pink, Plate 10RP 6/12 to Strong Red, Plate 2.5R 5/12, and veins being near a faint shade of Vivid Red, Plate 5R 5/13 where sunlight strikes petal surface.

*General color effect.*—Newly opened flower—between Deep Yellowish Pink, Plate 5R 6/11 and Vivid Red, Plate 5R 5/13. 3-days open—between Deep Pink, Plate 2.5R 6/11 and Strong Red, Plate 2.5R 5/12.

*Behavior.*—Drop off cleanly; during cold and wet weather, outer petals sometimes stick together and flower fails to open properly; drops of dew cause spotting by spot-bleaching, resulting in grayish translucent spots where sun strikes dew.

*Flower longevity.*—On bush in garden—3 or 4 days in October. Cut roses grown outdoors and kept at living-room temperatures—4 or 5 days in October.

*Reproductive Organs*

Stamens: Medium quantity; arranged irregularly about pistils; occasionally mixed with pistils.

Filaments: Variable length; from 5 to 10 mm. long; most with anthers. Color—yellow.

Anthers: Medium size; open at various times. Color—yellow.

Pollen: Moderately abundant. Color—yellow.

Pistils: Many.

Styles: Fairly even; medium length; medium caliper; loosely bunched.

Stigma: Color—White, or nearly so.

Ovaries: Usually all enclosed in calyx.

Hips: Usually globular; smooth; walls thick and fleshy. Color (at maturity)—orange.

Sepals: Permanent; moderately short; more or less straight; spear-shaped.

Seeds: Few; medium to large size for class.

*Plant*

Foliage:

*Leaves.*—Compound of 3 to 7 leaflets; normal quantity; from medium to large size; heavy; leathery; glossy.

*Leaflets.*—Shape—near elliptical, with apex from acute to acuminate. Base—from round to truncate (asymmetrical). Margin—both simply and doubly serrate.

*Color.*—Mature: upper surface—dark green; under surface—light gray-green. Young: upper surface—light green, with heavy overlay of dark red; under surface—light green, with heavy overlay of dark red over most of area, especially on veins.

*Rachis (the supporting stem of the compound leaf).*—Medium weight and caliper. Upper side—grooved; ridges lined with short stipitate glands. Under side—sparsely prickly.

*Stipules.*—Medium length; moderately narrow; with short points turning out at an angle of about 45°; sometimes recurved toward the stem.

*Disease resistance.*—Good resistance to powdery mildew as determined by comparison with a wide variety of garden roses grown under the same cultural conditions at Ontario, California.

Growth:

*Habit.*—Upright; tall; moderately branched.

*Growth.*—Vigorous.

*Canes.*—Moderately heavy caliper.

*Main stems.*—Color—gray green. Large prickles—several; medium length; with base of various length and width; color—brown. Small prickles—few; color—brown. Hairs—none.

*Branches.*—Color—gray-green. Large prickles—several; medium length; straight; with long, narrow base: color—brown. Small prickles—few; color—brown. Hairs—none.

*New shoots.*—Color—green, with red overlay. Large prickles—several; medium length; straight; with narrow base of medium length; color—reddish purple. Small prickles—few; color—reddish. Hairs—none.

We claim:

A new and distinct variety of rose plant of the grandiflora class, substantially as herein shown and described, characterized particularly as to novelty by the unique combination of vigorous, upright and tall habits of growth, distinctive shape, medium to large size and distinctive surface appearance of the foliage, a habit of producing the large majority of its flowers in both simple and compound clusters, medium to large size and attractive shape of the flowers, a distinctive and attractive general color tonality of the flowers corresponding to salmon or shrimp color, and good resistance of the foliage and stems to powdery mildew.

No references cited.